(12) United States Patent
Tao

(10) Patent No.: US 6,537,581 B2
(45) Date of Patent: Mar. 25, 2003

(54) COMPOSITIONS AND METHODS FOR TREATING EYE DISCOMFORT

(75) Inventor: Yuanjin Tao, Fremont, CA (US)

(73) Assignee: Theralife, Inc., Los Altos, CA (US)

( * ) Notice: Subject to any disclaimer, the term of this patent is extended or adjusted under 35 U.S.C. 154(b) by 0 days.

(21) Appl. No.: 09/872,403

(22) Filed: Jun. 1, 2001

(65) Prior Publication Data

US 2002/0009504 A1 Jan. 24, 2002

Related U.S. Application Data

(60) Provisional application No. 60/208,783, filed on Jun. 1, 2000.

(51) Int. Cl.$^7$ .................................................. A61K 9/14
(52) U.S. Cl. ........................ 424/489; 424/451; 424/464; 424/725; 424/732
(58) Field of Search ................................. 424/427, 489, 424/725, 732, 451, 464

(56) References Cited

U.S. PATENT DOCUMENTS

| | | | |
|---|---|---|---|
| 5,118,505 A | 6/1992 | Költringer |
| 5,149,521 A | 9/1992 | Hirose et al. |
| 5,240,732 A | 8/1993 | Ueda |
| 5,384,123 A | 1/1995 | Metsada |
| 5,411,733 A | 5/1995 | Hozumi et al. |
| 5,466,443 A | 11/1995 | Ho et al. |
| 5,466,452 A | 11/1995 | Whittle |
| 5,494,668 A | 2/1996 | Patwardhan |
| 5,547,671 A | 8/1996 | Duthinh |
| 5,585,101 A | 12/1996 | Portman |
| 5,595,743 A | 1/1997 | Wu |
| 5,707,630 A | 1/1998 | Morrow |
| 5,744,187 A | 4/1998 | Gaynor |
| 5,804,168 A | 9/1998 | Murad |
| 5,854,291 A | 12/1998 | Laughlin et al. |
| 5,856,361 A | 1/1999 | Holt et al. |
| 5,882,672 A | 3/1999 | Kojima et al. |
| 5,888,514 A | 3/1999 | Weisman |
| 5,895,652 A | 4/1999 | Giampapa |
| 5,904,924 A | 5/1999 | Gaynor et al. |
| 5,908,628 A | 6/1999 | Hou |
| 5,908,857 A | 6/1999 | Suzuki |
| 5,916,542 A | 6/1999 | Fossati |
| 5,916,565 A | 6/1999 | Rose et al. |
| 5,955,102 A | 9/1999 | Gorenbein et al. |
| 5,976,548 A | 11/1999 | Hsia et al. |
| 6,027,728 A | 2/2000 | Yuen |
| 6,030,980 A | 2/2000 | Suzuki |

FOREIGN PATENT DOCUMENTS

| | | |
|---|---|---|
| CN | 1207927 | 2/1999 |
| CN | 1207930 | 2/1999 |
| CN | 1216254 | 5/1999 |
| EP | 0 970 621 A1 | 1/2000 |
| WO | WO 98/33494 A1 | 8/1998 |

OTHER PUBLICATIONS

Botte et al., (1996) "Recurrent Carpal Tunnel Syndrome." *Hand Clin.* 12(4):731–743.

Bergqvist and Knave, (1994) "Eye discomfort and work with visual display terminals." *Scand. J. Work Environ. Health,* 20(1):27–33.

Borenstein, (1992) "Epidemiology, etiology, diagnostic evaluation, and treatment of low back pain." *Cur. Opin. Rheumatol* 4(2):226–232.

De Smet et al., (1995) "Value of Clinical Provacative Tests in Carpal Tunnel Syndrome." *Acta. Orthop. Belg.* 61(3):177–182.

Deyo and Phillips, (1996) "Low Back Pain" *Spine* 21:2826–2832.

Hikichi, T. et al., (1995) "Prevalence of dry eye in Japanese eye centers" *Graefes Arch. Clin. Exp. Ophthalmol.,* 223 (9):555–558.

Kirsner, R. S. and Federman, D.G., (1998) "Video Display Terminals: Risk of Electromagnetic Radiation" *South Med. J,* 91 (1):12–16.

Kuschner et al., (1992) "Tinel's Sign and Phalen's Test in Carpal Tunnel Syndrome." *Orthopedics,* 15(11):1297–1302.

Melhorn (1994) "CTD: Carpal Tunnel Syndrome, The Facts and Myths." *Kans. Med.* 95(9):189–192.

*Remington's Pharmaceutical Sciences,* 18th Edition, Mack Publishing (1990), pp. xv–xvi (Table of Contents.).

Salibello Nilsen, (1995) "Is there a typical VDT patient? A demographic analysis." *J. Am. Optom. Assoc.,* 66(8):479–483.

Sheedy, J.E., (1992) "Vision problems at video display terminals: a survey of optometrist"*J. Am. Optom. Assoc.,* 63 (10):687–692.

Sternback, (1999) "The Carpal Tunnel Syndrome." *J. Emerg. Med.* 17(3):519–523.

Szabo, (1998) "Carpal Tunnel Syndrome as a Repetitive Motion Disorder." *Clin. Orthop.* 351:78–89.

Database WPI, Week 200169, Derwent Publications, Ltd., London, GB; AN 2001–603094, XP002203915, J. Pang (Dec. 24, 1997) "Eyesight granule and its compounding process" and CN 1 168 277, abstract, one page.

Database WPI, Week 200114, Derwent Publications, Ltd., London, GB; AN 2001–123595, XP002203916, M. Huang (Apr. 2, 1997) "Yanming bag–soaking oral preparation for eye health care and its preparation" and CN 1 146 346, abstract, one page.

(List continued on next page.)

Primary Examiner—Thurman K. Page
Assistant Examiner—Robert M. Joynes
(74) *Attorney, Agent, or Firm*—Morrison & Foerster LLP

(57) ABSTRACT

Compositions and methods for treating eye discomfort are provided. The compositions comprise singly or in combination herbals, natural nutritional supplements, minerals and vitamins. Methods of making these compositions are also provided.

1 Claim, No Drawings

OTHER PUBLICATIONS

Database WPI, Week 20012, Derwent Publications, Ltd., London, GB; AN 2000–127221, XP002203917, Y. Ding E.A. (Dec. 2, 1998) "Granule preparation for trating near sightedness, and production process" and CN 1 200 287, abstract, one page.

Database WPI, Week 199423, Derwent Publications, Ltd., London, GB; AN 1994–184169, XP002203918, S. Bei E.A. (Sep. 8, 1993) "Nutritious liquid for eyesight–consists of extracts of cassia seed, fruit of lycium barbarum, mulberry flower head, vitamin A, vitamin C etc" and CN 1 075 878, abstract, one page.

Database WPI, Week 198250, Derwent Publications, Ltd., London, GB; AN 1982–07782j, XP002203919, Showa Kagaku (Nov. 4, 1982) "Pharmaceutical for eye diseases– comprises Dioscorea root, Gougiza, Flos Chysanthemi, Pueraria and dry raw gall bladder of carp" and JP 57–179121, abstract, one page.

Database EPODOC 'Online!, European Patent Office, The Hague, NL, XP002203914 abstract and KR 9 706 124 A, Bang Sung–Mo, (Apr. 24, 1997), abstract, one page.

COMPOSITIONS AND METHODS FOR TREATING EYE DISCOMFORT

CROSS-REFERENCE TO RELATED APPLICATIONS

This application claims the benefit of U.S. Provisional Application Serial No. 60/208,783, filed Jun. 1, 2000, hereby incorporated in its entirety by reference.

TECHNICAL FIELD

This invention relates to compositions and methods for treating eye disorders. More specifically, it relates to nutraceutical compositions for treating eye discomfort symptoms, and methods for treating these symptoms with said compositions.

BACKGROUND ART

One in five Americans suffers from discomfort of the eyes. One of the most common eye discomforts is due to dry eye condition. Dry eye conditions are characterized by ocular surface epithelium undergoing squamous metaplasia, loss of goblet cells, mucin deficiency and keratinization, leading to the clinical symptoms of dry eye syndrome. The advent of computer technology has accelerated the prevalence of vision disorders such as the dry eye syndromes. This is primarily due to the necessary use of video display terminals such as computer monitors.

The prevalence of dry eye discomfort in visual display terminal users and contact lens wearers is significantly higher than in non-visual display terminal users and non-contact lens wearers. It is suggested that dry eye is one of the most common ocular disorders encountered by physicians. Hijichi, T. et al., *Graefes Arch. Clin. Exp. Ophthalmol.* (1995), 233(9):555–8.

The correlation between eye discomfort symptoms generally and work with visual display terminals has been clearly documented. The occurrence of eye discomfort increases as the extent of work involving visual display terminals increases. Symptoms include sensitivity to light, smarting and gritting feeling of the eyes, and eye redness. Bergqvist and Knave, *Scand. J. Work Environ. Health* (1994), 20(1):27–33. It is estimated that between 75 and 88 percent of patients who use video display terminals regularly are likely to be symptomatic for visual problems. Salibello, C. and Nilsen, E., *J. Am. Optom. Assoc.* (1995), 66(8): 479–83. It has been found that, on the average, 14.25 percent of optometric patients present with symptoms primarily associated with the use of video display terminals, which translates into approximately 10 million cases annually in the U.S. population. Sheedy, J. E., *J. Am. Optom. Assoc.* (1992), 63(10):687–92.

The use of video display terminals in the workplace is growing rapidly. It was estimated that more than 100 million workers in the United States and Canada would be using computers daily by the year 2000. Kirsner, R. S. and Federman, D. G., *South Med. J.* (1998), 91(1):12–6. Therefore, it is reasonable to expect that there will be a significant increase in the prevalence of eye discomfort symptoms resulting from the use of computers.

Herbal remedies that are thought to be beneficial for improving visual functions generally are of unspecific efficacy for eye discomfort. For example, a composition containing bilberry has been indicated to improve night vision acuity, field of vision and adaptation to light. U.S. Pat. No. 5,955,102. It is not disclosed whether this composition would be beneficial to individuals suffering from more specific (and more prevalent) eye discomfort conditions such as the dry eye syndrome.

A composition that addresses the causes of dry eye syndrome and supports the body's natural tear formation is known. (HydroEye, ScienceBased Health, Carson City, Nev.). The ingredients in this composition include vitamins A, C and B-6, magnesium sulfate, mucin complex, cod liver oil and black currant oil.

Multinutrient formulations with eye-specific nutrients are known. (MaculaRx & MaculaRx Plus, ScienceBased Health, Carson City, Nev.). The ingredients include vitamins A, B-6, B-12, C and E, magnesium, selenium, zinc, carotenoids, taurine, N-acetyl cysteine, lipoic acid, inositol, bilberry extract and ginkgo biloba extract.

A multivitamin supplement with basic eye-specific nutrients is known. (Ocular Essentials, ScienceBased Health, Carson City, Nev.). Its ingredients include Vitamins A, B1, B2, B3, B5, B6, B12, C, D3, E and K, biotin, folic acid, boron, calcium, chromium, copper, iodine, magnesium, manganese, molybdenum, potassium, sodium, selenium, zinc, carotenoids, zeaxanthin and cryptoxanthin, taurine, and bilberry extract.

A formulation for providing eye health and nutritional support is known. (OculaRx, ScienceBased Health, Carson City, Nev.). Its ingredients include Vitamins A, B1, B2, B3, B5, B6, B12, C, D3 and E, biotin, folic acid, boron, calcium, chromium, copper, iodine, magnesium, manganses, molybdenum, phosphorus, selenium, zinc, bilberry extract, carotenoids, choline, ginkgo extract, grape seed extract, hesperidin bioflavonoid complex, lipoic acid, N-acetyl cysteine, rutin and taurine.

A composition for treating eye disorders is known. (Visianna Eye Refresher, Amino Foods Technologies, San Jose, Calif.). The ingredients in this formula include gochee berry extract (lycium barbarum L.), juhua (chrysanthemum morifolium Ramat), beta-carotene, vitamin E, ascorbic acid, riboflavin, zinc, copper, selenium and magnesium.

In view of the seriousness and prevalence of eye discomfort symptoms, and the corresponding need to alleviate said symptoms without significant side effects, it would be advantageous to have compositions and methods that are efficacious and safe to address this need. The invention described and claimed in this specification presents such compositions and methods.

All references cited herein, including patent applications and publications, are incorporated by reference in their entirety.

DISCLOSURE OF THE INVENTION

Compositions and methods for treating eye discomfort are provided. The compositions comprise substances in quantities that are effective in relieving eye discomfort. Methods of treating eye discomfort comprising administration of the claimed compositions are also provided.

Accordingly, in one aspect, the invention provides a composition for treating eye discomfort comprising a substance selected from the group consisting of a member of the botanical group poria cocos, a member of the botanical group Cassia, a member of the botanical group Morus, a member of the botanical group Dioscorea, a member of the botanical group officinale and a member of the botanical group Rehmannia.

In another aspect, the invention provides a composition for treating eye discomfort comprising 2 substances selected from the group consisting of a member of the botanical group poria cocos, a member of the botanical group Cassia, a member of the botanical group Morus, a member of the botanical group Dioscorea, a member of the botanical group officinale and a member of the botanical group Rehmannia.

In another aspect, the invention provides a composition for treating eye discomfort comprising 3 substances selected from the group consisting of a member of the botanical group poria cocos, a member of the botanical group Cassia, a member of the botanical group Morus, a member of the botanical group Dioscorea, a member of the botanical group officinale and a member of the botanical group Rehmannia.

In another aspect, the invention provides a composition for treating eye discomfort comprising 4 substances selected from the group consisting of a member of the botanical group poria cocos, a member of the botanical group Cassia, a member of the botanical group Morus, a member of the botanical group Dioscorea, a member of the botanical group officinale and a member of the botanical group Rehmannia.

In another aspect, the invention provides a composition for treating eye discomfort comprising 5 substances selected from the group consisting of a member of the botanical group poria cocos, a member of the botanical group Cassia, a member of the botanical group Morus, a member of the botanical group Dioscorea, a member of the botanical group officinale and a member of the botanical group Rehmannia.

In another aspect, the invention provides a composition for treating eye discomfort comprising a member of the botanical group poria cocos, a member of the botanical group Cassia, a member of the botanical group Morus, a member of the botanical group Dioscorea, a member of the botanical group officinale and a member of the botanical group Rehmannia.

In one embodiment, the invention provides a composition selected from the group consisting of the compositions of the aspects of the invention described in the preceding paragraphs, further comprising a substance selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc. For example, a composition may comprise a member of the botanical group Rehmannia (such as shudihaung) and a member of the botanical group Lycium (gouqizhi). In another example, a composition may comprise a member of the botanical group Chrysanthemum (such as juhua) and a member of the botanical group Morus (such as sang ye).

In one embodiment, the invention provides a composition selected from the group consisting of the compositions of the aspects of the invention described in the preceding paragraphs, further comprising 2 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 3 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 4 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 5 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 6 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 7 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 8 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 9 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 10 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 11 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 12 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 13 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 14 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 15 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising 16 substances selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In one embodiment, the invention provides a composition selected from the group consisting of the compositions of the aspects of the invention described in the preceding paragraphs, further comprising a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc.

In various embodiments of the compositions of the invention described in the preceding and following paragraphs, the member of the botanical group poria cocos may be fuling, the member of the botanical group Cassia may be jueminzi, the member of the botanical group Morus may be sang ye, the member of the botanical grouop Dioscorea may be shanyao, the member of the botanical group officinale may be shanzhuyu, the member of the botanical group Rehmannia may be shudihaung, the member of the botanical group Vaccinium may be bilberry, the member of the botanical group Salvia may be danshen, the member of the botanical group Lycium may be gouqizhi, the member of the botanical group Chrysanthemum may be juhua, the member of the botanical group Tribulus may be baijili, the member of the botanical group Eriocaulon may be gujincao, the member of the botanical group *Paeonia suffruticosa* may be mudanpi, and/or the member of the botanical group Alisma may be zexie. Accordingly, in one embodiment, the invention provides a composition for treating eye discomfort comprising fuling, jueminzi, sang ye, shanyao, shanzhuyu, shudihaung, bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

Accordingly, in one aspect, the invention provides a composition for treating eye discomfort comprising a substance selected from the group consisting of fuling, jueminzi, sang ye, shanyao, shanzhuyu and shudihaung.

In another aspect, the invention provides a composition for treating eye discomfort comprising 2 substances selected from the group consisting of fuling, jueminzi, sang ye, shanyao, shanzhuyu and shudihaung.

In another aspect, the invention provides a composition for treating eye discomfort comprising 3 substances selected from the group consisting of fuling, jueminzi, sang ye, shanyao, shanzhuyu and shudihaung.

In another aspect, the invention provides a composition for treating eye discomfort comprising 4 substances selected from the group consisting of fuling, jueminzi, sang ye, shanyao, shanzhuyu and shudihaung.

In another aspect, the invention provides a composition for treating eye discomfort comprising 5 substances selected from the group consisting of fuling, jueminzi, sang ye, shanyao, shanzhuyu and shudihaung.

In yet another aspect, the invention provides a composition for treating eye discomfort comprising fuling, jueminzi, sang ye, shanyao, shanzhuyu and shudihaung.

In one embodiment, the invention provides a composition selected from the group consisting of the compositions of the aspects of the invention described in the preceding paragraphs, further comprising a substance selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 2 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 3 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 4 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 5 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 6 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 7 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 8 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 9 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 10 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 11 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 12 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 13 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 14 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 15 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In another embodiment, the invention provides a composition selected from the group consisting of the compositions of the aspects of the invention described in the preceding paragraphs, further comprising 16 substances selected from the group consisting of bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In yet another embodiment, the invention provides a composition selected from the group consisting of the compositions of the aspects of the invention described in the preceding paragraphs, further comprising bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

In one aspect, the invention provides a method of treating eye discomfort comprising administering to the individual an effective amount of a composition selected from the group consisting of the compositions of the aspects and embodiments of the invention described in the preceding paragraphs, whereby eye discomfort is treated. In some embodiments, said eye discomfort is a condition selected from the group consisting of dry eye syndrome, itchy and red eye condition, eye fatigue, and eye sandiness and soreness.

In another aspect, the invention provides a method of making a composition for treating eye discomfort, said method comprising combining at least two (preferably 2, 3, 4, 5 or 6) substances (preferably in an effective amount) selected from the group consisting of a member of the botanical group poria cocos, a member of the botanical group Cassia, a member of the botanical group Morus, a member of the botanical group Dioscorea, a member of the botanical group officinale and a member of the botanical group Rehmannia. In some embodiments of these methods, said at least two substances are combined with at least one (preferably 1, 2, 3, 4, 5, 6, 7, 8, 9, 10, 11, 12, 13, 14, 15, 16, 17) substance (preferably an effective amount) selected from the group consisting of a member of the botanical group Vaccinium, a member of the botanical group Salvia, a member of the botanical group Lycium, a member of the botanical group Chrysanthemum, a member of the botanical group Tribulus, beta-carotene, copper, a member of the botanical group Eriocaulon, magnesium, a member of the botanical group *Paeonia suffruticosa,* rice flour powder, selenium, vitamin B-2, vitamin C, vitamin E, a member of the botanical group Alisma and zinc. In some embodiments, said combining is by mixing (such as by stirring, agitation or vibration). In some embodiments, the substances are packaged in the form of capsules, preferably in size "0", "00", "000", "1", "2""3" or "4." In yet other embodiments, the substances are combined in powder form, preferably to at least 30%, 60%, or 90% mixture consistency, or to homogeneity.

MODES FOR CARRYING OUT THE INVENTION

The present invention discloses compositions comprising single or multiple substances that are effective and safe for treating symptoms of eye discomfort. The invention further provides methods of treating eye discomfort using the disclosed compositions. Methods of making these compositions are also provided.

Definitions

The term "treating," "treatment," and variations thereof, as used in this specification, refers to an approach for obtaining beneficial or desired physiological results, which may be established clinically. For purposes of this invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of the condition or symptoms, and remission (whether partial or total), whether detectable or undetectable. The term "palliation", and variations thereof, as used herein, means that the extent and/or undesirable manifestations of a physiological condition or symptom are lessened and/or time course of the progression is slowed or lengthened, as compared to not administering compositions of the present invention.

A "treatment effect" or "therapeutic effect" is manifested if there is a change in the condition being treated, as measured by the criteria constituting the definition of the terms "treating" and "treatment." There is a "change" in the condition being treated if there is at least 10% improvement, preferably at least 25%, more preferably at least 50%, even more preferably at least 75%, and most preferably at least 100%. The change can be based on improvements in the severity of the treated condition in an individual, or on a difference in the frequency of improved conditions in populations of individuals with and without treatment with the compositions of the present invention.

An "effective amount" is an amount of a composition or substance(s) sufficient to effect beneficial or desired results in the treatment of eye discomfort after one or more administrations of that amount. An effective amount can be administered in one administration, or through multiple administrations of an amount that total an effective amount, preferably within a 24-hour period. It can be determined using standard clinical procedures for determining appropriate amounts and timing of administration. It is understood that the "effective amount" can be the result of empirical and/or individualized (case-by-case) determination on the part of the treating health care professional and/or individual.

"Eye discomfort," as used herein, refers to symptoms involving the eye that prevent the normal functioning or use of the eye. These symptoms can be those presently indicated as manifestations or any condition that an individual finds to be non-conducive to the optimal or normal use of the eye. Such symptoms include, but are not limited to, burning, irritation, dryness, redness, excess tearing, blurred vision, difficulty with visual focusing, eye fatigue, soreness, eye strain and/or watery eye, including such symptoms that are due to contact lens use.

"Individual," as used herein, refers to a vertebrate, preferably a mammal, more preferably a human.

A "botanical group," as used herein, refers to a group of botanical entities that are capable of providing similar physiological effect(s) in the compositions of the invention. These botanical entities may or may not belong to the same botanical classification (such as genus, family).

"Fuling," as used herein, refers to extracts of fuling. It is also known as sclerotium poriae cocos and poria cocos (Schw.) wolf. A member of the botanical group poria cocos is a substance that is capable of providing a similar physiological effect(s) as that provided by fuling in the compositions of the invention, and is preferably selected from a group comprising *Poria cocos* (schw.) wolf.; *Sclerotium poriae cocos.*

"Jueminzi," as used herein, refers to extracts of jueminzi. It is also known as semen cassiae and cossia obtusifolia L. A member of the botanical group Cassia is a substance that is capable of providing a similar physiological effect(s) as that provided by jueminzi in the compositions of the invention, and is preferably selected from a group comprising *Cassia obtusifolia* L.; *Cassia tora* L.; *Semen cassiae; Senna tora; Cassia tora* auct. non; *Emelista tora; Emelista tora sensu; Cassia tora; Cassia obtusifolia; Cassia tora* auct. Non; *Emelista tora; Emelista tora sensu; Semen obtusifolia.*

"Sang ye," as used herein, refers to extracts of sang ye. It is also known as folium mori albae and morus alba L. A member of the botanical group Morus is a substance that is capable of providing a similar physiological effect(s) as that provided by sang ye in the compositions of the invention, and is preferably selected from a group comprising *Morus Folium mori albae; Morus alba* L.; *Morus australis; Morus australis* Poir; *Morus mongolica* Schneid; *Morus cathayana* Hemsl.; *Morus laevigata* wall; *Morus acidosa* (Griff.); *Morus alba stylosa* ((Ser.)Bur.); *Morus indica* (non L.); *Morus stylosa* (Ser.); *Morus alba; Morus alba* f. *tatarica; Mortus alba* var. *constantinopolitana; Morus alba* var. *multicaulis; Morus alba* var. *stylosa; Morus alba* var. *tatarica; Morus constantinopolitana; Morus multicaulis; Morus tatarica.*

"Shanyao," as used herein, refers to extracts of shanyao. It is also known as radix dioscoreae oppositae and dioscorea opposita Thunb. A member of the botanical group Dioscorea is a substance that is capable of providing a similar physiological effect(s) as that provided by shanyao in the compositions of the invention, and is preferably selected from a group comprising *Radix dioscoreae oppositae; Dioscorea batatas; Dioscorea opposita* Thunb; *Dioscorea batatas* Decne.; *Dioscorea japonica* Thunb.; *Dioscorea divaricata; Dioscorea opposita* (Thunb.).

"Shanzhuyu," as used herein, refers to extracts of shanzhuyu. It is also known as fructus corni officinalis and cornus officinalis sieb. A member of the botanical group officinale is a substance that is capable of providing a similar physiological effect(s) as that provided by shanzhuyu in the compositions of the invention, and is preferably selected from a group comprising *Fructus corni officinalis; Cornus officalis* Sieb. et. Zucc.; *Macrocarpium officinale* (Sieb. et Zucc) Nakai.

"Shudihaung," as used herein, refers to extracts of shudihaung. It is also known as radix rehmanniae glutinosae conquitae and rehmannia glutinosa (Gaertn) Libosch. A member of the botanical group Rehmannia is a substance that is capable of providing a similar physiological effect(s) as that provided by shudihaung in the compositions of the invention, and is preferably selected from a group comprising *Radix rehmanniae; Radix rehmanniae glutinosae conquitae; Rehmannia glutinosa* (Gaertn) Libosch., f. hueichinggensis (Chao et Schih) Hsiao; *Rehmannia glutinosa* (Gaertn) Libosch; *Rehmannia glutinosa* (Gaertn) Libosch. var. *lutea Makino,* f. purpurea Makino; *Rehmannia chinensis; Digitalis glutinosa.*

"Bilberry," as used herein, refers to extracts of bilberry. It is also known as vaccinium myrtillus. A member of the botanical group Vaccinium is a substance that is capable of providing a similar physiological effect(s) as that provided by bilberry in the compositions of the invention, and is preferably selected from a group comprising *Vaccinium myrtillus; Vaccinium frondosum*

"Danshen," as used herein, refers to extracts of danshen. It is also known as radix salviae miltiorrhizae and salvia miltiorrhiza Bge. A member of the botanical group salvia is a substance that is capable of providing a similar physiological effect(s) as that provided by danshen in the compositions of the invention, and is preferably selected from a group comprising *Radix salviae miltiorrhizae; Salvia miltiorrhiza; Salviae multiorrhiza* Bge; *Salvia bowleyana* Dunn; *Salvia przewalskii* Maxim.; *Salvia przewalskii* Maxim. var. *mandarinorum* (Diels) Stib.; *Salvia yunnannensis* C. H. Wright; *Salvia kiaometiensis* Levl., f. *pubescensis; Salvia miltiorrhiza* Bunge var. *alba* C. Y. Wu et H. W. Li. mss.; *Salvia digitaloides* Diels; *Salvia trijuga* Diels; *Salvia plectranthoides* Griff.

"Gouqizhi," as used herein, refers to extracts of gouqizhi. It is also known as fructus lycii and lycium barbarum L. A member of the botanical group Lycium is a substance that is capable of providing a similar physiological effect(s) as that provided by gouqizhi in the compositions of the invention, and is preferably selected from a group comprising *Fructus lycii; Lycium barbarum* L.; *Lycium chinense* Mill.; *Lycium turcomanicum* Turcz; *Lycium potaninii* Pojank; *Lycium dasystemum* Pojank; *Lycium europaeum* (non L.); *Lycium halimifolium* (Mill.); *Lycium lanceolatum* (Veillard.); *Lycium megistocarpum* (Dun.); *Lycium ovatum.; Lycium subglobosum.; Lycium trewianum.* L. vu; *Lycium europeum; Lycium halamifolium; Lycium halmifolium; Lycium vulgare.*

"Juhua," as used herein, refers to extracts of juhua. It is also known as *Flos chrysanthemi morifolii* and chrysanthemum morifolium Ramat. A member of the botanical group Chrysanthemum is a substance that is capable of providing a similar physiological effect(s) as that provided by juhua in the compositions of the invention, and is preferably selected from a group comprising *Flos chrysanthemi morifolii; Chrysanthemum morifolium* Ramat.; *Chrysanthemum sinense; Chrysanthemum x morifolium* (Ramat.); *Chrysanthemum indicum; Chrysanthemum x morifolium; Chrysanthemum indicum x sinense; Chrysanthemum morifolium; Chrysanthemum stipulaceum; Dendranthema x morifolium* (Tzvelev.); *Dendranthema indicum; Dendranthema x grandiflorum; Gnaphalium indicum; Gnaphalium indicum* auct. Non.

"Baijili," as used herein, refers to extracts of baijili. It is also known as fructus tribuli terrestris and tribulus terrestris L. A member of the botanical group Tribulus is a substance that is capable of providing a similar physiological effect(s) as that provided by baijili in the compositions of the invention, and is preferably selected from a group comprising *Fructus tribuli terrestris; Tribulus terrestris* L; *Atriplex centralasiatica; Atriplex sibirica* L; *Pedalium murex; Tribulus terrestes; Tribulus terrestrus.*

"Beta-carotene," as used herein, refers to the form(s) of Vitamin A known to persons of skill in the art as such.

"Copper," as used herein, refers to the form(s) of the mineral known to persons of skill in the art to be therapeutically effective in the body of the individual. It is preferably provided as copper gluconate.

"Gujincao," as used herein, refers to extracts of gujincao. It is also known as eriocaulon sieboldtianum S. A member of the botanical group Eriocaulon is a substance that is capable of providing a similar physiological effect(s) as that provided by gujincao in the compositions of the invention, and is preferably selected from a group comprising *Eriocaulon buergerianum* Koern.; *Eriocaulon sieboldtianum* Sieh. et Zucc. Ex Steud; *Eriocaulon sieboldtianum* S. et Z.; *Eriocaulon sieboldianum; Eriocaulon saxangulara* L.; *Eriocaulon wallichianum* Mart.

"Magnesium," as used herein, refers to the form(s) of the mineral known to persons of skill in the art to be therapeutically effective in the body of the individual. It is preferably provided as magnesium stearate NF.

"Mudanpi," as used herein, refers to extracts of mudanpi. It is also known as cortex moutan radicis and paeonia suffruticosa Andr. A member of the botanical group *Paeonia suffruticosa* is a substance that is capable of providing a similar physiological effect(s) as that provided by mudanpi in the compositions of the invention, and is preferably selected from a group comprising *Cortex moutan radicis; Paeonia suffruticosa; Paeonia suffruticosa* Andr.; *Paeonia suffruticosa* Andr. var. *spontanea* Rehd.; *Paeonia suffruticosa* Andr. Var. *papaveracea* (Andr.) Kerner; *Paeonia papaveracea* Andr.; *Paeonia lutea* Franch.; *Paeonia szechuanica* Fang; *Paeonia moutan.* Sims.; *Paeonia moutan; Paeonia arborea.*

"Rice flour powder," as used herein, refers to the additive known to persons of skill in the art as such.

"Selenium," as used herein, refers to the form(s) of the mineral known to persons of skill in the art to be therapeutically effective in the body of the individual. It is preferably provided as selenium aminoate.

"Vitamin B-2," as used herein, refers to the riboflavin member of the Vitamin B series or complex.

"Vitamin C," as used herein, refers to ascorbic acid and salts thereof.

"Vitamin E," as used herein, refers to D alpha-tocopherol, preferably in its succinate form.

"Zexie," as used herein, refers to extracts of zexie. It is also known as rhizoma alismatis orientalitis and alisma plantagoaquatica L. A member of the botanical group Alisma is a substance that is capable of providing a similar physiological effect(s) as that provided by zexie in the compositions of the invention, and is preferably selected from a group comprising *Rhizoma alismatis orientalitis; Alisma plantagoaquatica* L; *Alisma plantago-aquatica* L. var. *orientate* Sam.; *Alisma orientalitis* (Sam.) Juzep.; *Alisma parviflorum* (Pursh.); *Alisma subcordatum* (Raf.); *Alisma triviale* (Pursh.); *Alisma brevipes; Alisma plantago; Alisma plantago-aquatica* ssp. Brevipes; *Alisma plantago-aquatica* ssp. subcordatum; *Alisma plantago-aquatica* var. *americanum; Alisma plantago-aquatica* var. *brevipes; Alisma plantago-aquatica* var. *parviflorum.*

"Zinc," as used herein, refers to the form(s) of the mineral known to persons of skill in the art to be therapeutically effective in the body of the individual. It is preferably provided as zinc gluconate.

"Extract," as used herein, refers to the substances obtained from the specified source plant, or parts thereof (for e.g., root, bark, leaves). Any method of extraction that yields extracts that retain the biological activity of the substances contained in the extract source can be used to produce extracts used in this invention. Preferably, the ingredients of the compositions of the present invention are extracted as an aqueous solution. The extraction is preferably performed under conditions of high pressure, preferably from 0.5 to 12 bar, more preferably 1 to 10 bar, most preferably 3 to 7 bar, and preferably at elevated temperatures (preferably within a range of 15° C. to 120° C., more preferably 30° C. to 100° C., most preferably 45° C. to 75° C.). The extract is preferably treated to yield a form suitable for mixing of two or more substances. The form is preferably a dried powder. The powder form is yielded from preferably at least about a 1:10, more preferably at least about a 1:8, most preferably at least about a 1:5 concentrate of the starting solution. Concentration to powder form is preferably achieved by evaporation to yield a dried powder form. The extracts used in this invention can also be obtained from commercial sources such as Sun Ten Laboratories (Irvine, Calif.), Qualiherb (Cerritos, Calif.), Mayway (Oakland, Calif.), Ming Tong Herb (Oakland, Calif.) and Acta (Sunnyvale, Calif.). It is understood that any method or conditions known in the art to yield extracts comparable in therapeutic effectiveness to those produced by the preceding preferred extraction method can be used for the purposes of this invention.

Formulation of the Compositions

Each substance contained in the compositions provided by this invention is provided in an amount that lies within specific quantitative ranges herein disclosed to be effective for treating eye discomfort.

According to the present invention, an effective amount of a composition comprises preferably from 12 to 200 mg, more preferably 25 to 150 mg, most preferably 50 to 100 mg of a member of the botanical group poria cocos (such as fuling); preferably from 5 to 100 mg, more preferably 25 to 75 mg, most preferably 50 to 60 mg of a member of the botanical group Cassia (such as jueminzi); preferably 35 to 400 mg, more preferably 75 to 300, most preferably 125 to 225 mg of a member of the botanical group Morus (such as sang ye); 12 to 200 mg, more preferably 25 to 150 mg, most preferably 50 to 100 mg of a member of the botanical group Dioscorea (such as shanyao); 12 to 200 mg, more preferably 25 to 150 mg, most preferably 50 to 100 mg of a member of the botanical group officinale (such as shanzhuyu); and/or preferably 25 to 1200 mg, more preferably 75 to 1000 mg, most preferably 250 to 750 mg of a member of the botanical group Rehmannia (such as shudihaung).

In the various embodiments of the invention, the compositions further comprise from 12 to 200 mg, more preferably 25 to 150 mg, most preferably 50 to 100 mg of a member of the botanical group Vaccinium (such as bilberry); 12 to 200 mg, more preferably 25 to 150 mg, most preferably 50 to 100 mg of a member of the botanical group Salvia (such as danshen); preferably 75 to 1200 mg, more preferably 200 to 1000 mg, most preferably 350 to 750 mg of a member of the botanical group Lycium (such as gouqizhi); preferably 50 to 700 mg, more preferably 150 to 500 mg, most preferably 300 to 400 mg of a member of the botanical group Chrysanthemum (such as juhua); 12 to 200 mg, more preferably 25 to 150 mg, most preferably 50 to 100 mg of a member of the botanical group Tribulus (such as baijili); preferably 15 to 250 mg, more preferably 50 to 150 mg, most preferably 75 to 100 mg beta-carotene, preferably 5 to 80 mg, more preferably 15 to 60 mg, most preferably 40 to 50 mg copper gluconate; preferably 5 to 100 mg, more preferably 20 to 75 mg, most preferably 35 to 50 mg of a member of the botanical group Eriocaulon (such as gujingcao); preferably 7 to 120 mg, more preferably 25 to 100 mg, most preferably 50 to 75 mg magnesium stearate NF; 12 to 200 mg, more preferably 25 to 150 mg, most preferably 50 to 100 mg of a member of the botanical group *Paeonia suffruticosa* (such as mudanpi); preferably 5 to 100 mg, more preferably 25 to 75 mg, most preferably 50 to 60 mg rice flour powder; preferably 4 to 80 mg, more preferably 12 to 65 mg, most preferably 25 to 50 mg selenium aminoate; preferably 3 to 75 mg, more preferably 12 to 50 mg, most preferably 25 to 40 mg vitamin B-2; preferably 40 to 800 mg, more preferably 120 to 600 mg, most preferably 250 to 500 mg vitamin C; preferably 50 to 850 mg, more preferably 150 to 650 mg, most preferably 300 to 500 mg vitamin E; 12 to 200 mg, more preferably 25 to 150 mg, most preferably 50 to 100 mg of a member of the botanical group Alisma (such as zexie); and/or preferably 40 to 600 mg, more preferably 120 to 500 mg, most preferably 250 to 400 mg zinc gluconate.

For example, a composition may comprise preferably 25 to 1200 mg, more preferably 75 to 1000 mg, most preferably 250 to 750 mg of a member of the botanical group Rehmannia (such as shudihaung) and preferably 75 to 1200 mg, more preferably 200 to 1000 mg, most preferably 350 to 750 mg of a member of the botanical group Lycium (gouqizhi). In another example, a composition may comprise preferably 50 to 700 mg, more preferably 150 to 500 mg, most preferably 300 to 400 mg of a member of the botanical group Chrysanthemum (such as juhua) and preferably 35 to 400 mg, more preferably 75 to 300, most preferably 125 to 225 mg of a member of the botanical group Morus (such as sang ye).

Selection of suitable members of a particular botanical group to be included in a composition can be achieved using methods known in the art. For example, a suitable member of the botanical group Cassia would be expected to be capable of providing a similar activity and/or function as that provided by jueminzi in a composition of the invention. Such a member can be selected based on, for example, whether it is known, shown and/or suspected to possess said similar activity and/or function. Thus, for example, a determination of whether a candidate substance can be a member of the botanical group Cassia can be done based on, for example, a similar pharmacological or medicinal classification for both the candidate substance and jueminzi. However, the activity and/or function provided by a particular substance, such as jueminzi, need not be identified or specified. A determination of whether a candidate substance can be a member of a particular botanical group, for example the Cassia group, can also be empirical, for example, by substituting said candidate substance for jueminzi in a composition, and assessing the relevant therapeutic effect(s) of the composition. Such a determination can be done using methods and techniques known in the art.

According to this invention, the compositions can be formulated in whatever physical form that retains the efficacy of the composition for treating eye discomfort. Preferably, the compositions are packaged in the form of capsules. The capsules are preferably of size "0", "00", "000", "1", "2", "3" or "4." A preferred method for packaging into capsules involves mixing substances (extracts, vitamin and minerals) that are preferably in powder form. The substances are preferably mixed to at least 30%, more preferably to at least 60%, even more preferably to at least 90% mixture consistency, and most preferably to homogeneity. The substances in powder form are provided in the initial mixture at ratios according to the effective quantities disclosed above. Methods for mixing the substances are known in the art, including, but not limited to, stirring, agitation or vibration achieved manually or through the aid of a machine. A preferred mixing machine is a V-mixer, preferably of 100 to 1400-liter size, more preferably of 150 to 1300-liter size, and most preferably of 200 to 1200-liter size. Preferably, the resulting powder mixture is filtered to screen out particulates (i.e., anything that a person of skill in the art would recognize to be larger than powder size). A preferred filter is a ¹⁄₂₀-inch particle size filter. Preferably, the filtered mixture is packaged into capsules according to the weight desired for each capsule. Preferably, the capsule is of size "00". The weight of mixture per capsule is preferably from 5 mg to 1000 mg, more preferably 100 mg to 800 mg, even more preferably 400 mg to 700 mg. It is understood that other physical forms of the compositions of this invention suitable for administration to an individual can also be used, including, for example, tablets, salves or liquids, as long as the compositions can be delivered to the target tissues in the body where the compositions in the preferred form described above exert their effects.

The ingredients of the compositions can be mixed with pharmaceutically acceptable solvents, excipients and/or filler substances. These materials are known in the art, and are described in sources such as *Remington's Pharmaceutical Sciences,* 18th Edition, Mack Publishing (1990).

Administration of Compositions

Compositions in any of the physical forms described above can be administered by any method known to one of skill in the art, but oral administration is preferred. The compositions are preferably administered in capsule form.

An effective amount of a composition is provided preferably in from 1 to 8 administrations, more preferably in from 2 to 6 administrations, and most preferably in from 3 to 5 administrations. Administration of an effective amount is preferably completed within 24 hours. A composition can be ingested alone, or with any other substance, such as a liquid, that aids ingestion of the compositions. Ingestion of the compositions can be before or after food consumption.

EXAMPLES

Example 1

An Illustrative Example of the Formulation of A Single "00" Capsule, and the Production Thereof A composition shown to be effective for treating eye discomfort contained substances in the indicated quantities as listed in Table 1.

TABLE I

| SUBSTANCE [Commercial source] | AMOUNT (mg) |
| --- | --- |
| Fuling [Qualiherb, Cerritos, CA] | 16.7 |
| Jueminzi [Qualiherb, Cerritos, CA] | 8.3 |
| Sang ye [Qualiherb, Cerritos, CA] | 33.3 |
| Shanyao [Qualiherb, Cerritos, CA] | 16.7 |
| Shanzhuyu [Mayway, Oakland, CA] | 16.7 |
| Shudihaung [Qualiherb, Cerritos, CA] | 100.0 |
| Bilberry [Acta, Sunnyvale, CA] | 16.7 |
| Danshen [Qualiherb, Cerritos, CA] | 16.7 |
| Gouqizhi [Qualiherb, Cerritos, CA] | 100.0 |
| Juhua [Qualiherb, Cerritos, CA] | 66.7 |
| Baijili [Qualiherb, Cerritos, CA] | 16.7 |
| Beta-carotene [Acta, Sunnyvale, CA] | 22.5 |
| Copper gluconate [Acta, Sunnyvale, CA] | 7.1 |
| Gujincao [Qualiherb, Cerritos, CA] | 8.3 |
| Magnesium stearate NF [Acta, Sunnyvale, CA] | 10.0 |

TABLE I-continued

| SUBSTANCE [Commercial source] | AMOUNT (mg) |
|---|---|
| Mudanpi [Qualiherb, Cerritos, CA] | 16.7 |
| Rice flour powder [Acta, Sunnyvale, CA] | 8.3 |
| Seleniuum aminoate [Acta, Sunnyvale, CA] | 6.7 |
| Vitamin B-2 (riboflavin) [Acta, Sunnyvale, CA] | 5.0 |
| Vitamin C (ascorbic acid) [Acta, Sunnyvale, CA] | 66.7 |
| Vitamin E (D Alpha-tocopherol succinate) [Acta, Sunnyvale, CA] | 76.0 |
| Zexie [Acta, Sunnyvale, CA] | 16.7 |
| Zinc gluconate [Acta, Sunnyvale, CA] | 57.7 |

Capsules containing the composition above were manufactured according to the method used by the commercial manufacturer, Acta (Sunnyvale, Calif.). Briefly, the substances listed above, in powder form and obtained from the commercial sources indicated, were mixed in input amounts in accordance to the ratio of the substances in the composition as a whole. Mixing was accomplished with a V-mixer, grinding for 15 to 30 minutes, at a speed of 15 to 30 rpm (rounds per minute), to produce a homogenous mixture of the input substances. Particulates (non-powder forms) were then filtered out with a 1/20-inch particle size filter that separated particulates from the powder. 694.97 mg of the filtered mixture was then packaged into each size "00" capsule.

Example 2

Illustrative Example of Treatment of Dry Eye Condition 10 individuals with dry eye symptom were treated with the composition exemplified in Example 1. They were instructed to fill out a clinical questionnaire to assess efficacy of treatment with the composition over time. The individuals were administered the composition for the duration and in the amount (capsules/day) as indicated in Table 2.

TABLE 2

| | Dosage Amount | | | | | |
|---|---|---|---|---|---|---|
| Individual No. | Day 3–5 (capsules/day) | Day 5–7 (capsules/day) | Day 8–14 (capsules/day) | Day 15–21 (capsules/day) | Day 22–28 (capsules/day) | Day 29–35 (capsules/day) |
| 1 | 2 | 2 | 2 | 2 | 2 | |
| 2 | 6 | 6 | 2 | 1 | 1 | 1 |
| 3 | 1 | 1 | 1 | 1 | 1 | 1 |
| 4 | 2 | 2 | 2 | 2 | 2 | 2 |
| 5 | 1 | 1 | 1 | 1 | 1 | 1 |
| 6 | 6 | 6 | 6 | 6 | 6 | 6 |
| 7 | 4 | 4 | 4 | 4 | 4 | |
| 8 | 4 | 4 | 4 | 4 | 4 | |
| 9 | 4 | 4 | 4 | 4 | 4 | |
| 10 | 4 | 4 | 4 | 4 | 4 | |

The results of the study are summarized in Table 3.

Severity of dry eye symptom was graded on a scale of 0 to 3. 0 was defined as normal eye condition, 1 was occasional symptoms, 2 was frequent symptoms and 3 was constant dry eye symptoms. Individuals were instructed to assess amount of tear production by their eyes as a primary indication of dry eye condition.

TABLE 3

| | Severity of Dry Eye Condition | | | | | | | |
|---|---|---|---|---|---|---|---|---|
| Individual No. | Before use | Day 3–5 | Day 5–7 | Day 8–14 | Day 15–21 | Day 22–28 | Day 29–35 | Day 36–42 |
| 1 | 2 | 2 | 1 | 1 | 1 | 1 | 0 | 0 |
| 2 | 3 | 2 | 2 | 1 | 1 | 1 | 1 | 0 |
| 3 | 3 | 2 | 2 | 1 | 1 | 1 | 1 | 0 |
| 4 | 3 | 3 | 3 | 2 | 1 | 1 | 1 | 0 |
| 5 | 3 | 2 | 2 | 1 | 1 | 1 | 1 | 1 |
| 6 | 3 | 2 | 2 | 1 | 1 | 1 | 1 | 0 |
| 7 | 3 | 3 | 2 | 1 | 1 | 1 | | |
| 8 | 2 | 2 | 1 | 1 | 1 | | | |
| 9 | 3 | 3 | 2 | 1 | | | | |
| 10 | 3 | 3 | 2 | 1 | 1 | 1 | | |

The results show a clear and significant decrease, and in some cases complete clearance, of dry eye symptoms following the administration of the composition of Example 1.

Example 3

Illustrative Example of Treatment of Eye Strain/Fatigue

Eight of the individuals of Example 2 were also assessed for eye strain/fatigue conditions. Results are summarized in Table 4.

Severity of eye strain/fatigue was graded on a scale of 0 to 3. 0 was defined as normal eye condition, 1 was occasional symptoms, 2 was frequent symptoms and 3 was constant eye strain/fatigue. Individuals were instructed to assess "burning" feeling and "sandy grittiness" of the eyes as primary indications of eye strain/fatigue.

The results show a clear and significant improvement, and in some cases complete clearance, of eye strain/fatigue in individuals administered the composition described in Example 1.

Example 4

Illustrative Example of Treatment of Eye Soreness

Seven of the individuals of Example 2 were also assessed for eye soreness. Results are summarized in Table 5.

Severity of eye soreness was graded on a scale of 0 to 3. 0 was defined as normal eye condition, 1 was occasional symptoms, 2 was frequent symptoms and 3 was constant eye soreness. Individuals were instructed to assess "pain-like" sensations of the eyes as primary indications of eye soreness.

TABLE 4

Severity of Eye Strain/Fatigue

| Individual No. | Before use | Day 3–5 | Day 5–7 | Day 8–14 | Day 15–21 | Day 22–28 | Day 29–35 | Day 36–42 |
|---|---|---|---|---|---|---|---|---|
| 1 | 2 | 2 | 1 | 1 | 1 | 1 | 0 | 0 |
| 2 | 3 | 2 | 2 | 1 | 1 | 1 | 1 | 0 |
| 3 | 3 | 2 | 2 | 1 | 1 | 1 | 1 | 0 |
| 4 | | | | | | | | |
| 5 | | | | | | | | |
| 6 | 3 | 2 | 2 | 1 | 1 | 1 | 1 | 0 |
| 7 | 3 | 3 | 2 | 1 | 1 | 1 | | |
| 8 | 2 | 2 | 1 | 1 | 1 | | | |
| 9 | 3 | 3 | 2 | 1 | | | | |
| 10 | 3 | 3 | 2 | 1 | 1 | 1 | | |

TABLE 5

Severity of Eye Soreness

| Individual No. | Before use | Day 3–5 | Day 5–7 | Day 8–14 | Day 15–21 | Day 22–28 | Day 29–35 | Day 36–42 |
|---|---|---|---|---|---|---|---|---|
| 1 | 2 | 2 | 1 | 1 | 1 | 1 | 0 | 0 |
| 2 | 3 | 2 | 2 | 1 | 1 | 1 | 1 | 0 |
| 3 | 3 | 2 | 2 | 1 | 1 | 1 | 1 | 0 |
| 4 | | | | | | | | |
| 5 | | | | | | | | |
| 6 | 3 | 2 | 2 | 1 | 1 | 1 | 1 | 0 |
| 7 | | | | | | | | |
| 8 | 2 | 2 | 1 | 1 | 1 | | | |
| 9 | 3 | 3 | 2 | 1 | | | | |
| 10 | 3 | 3 | 2 | 1 | 1 | 1 | | |

The results show a clear and significant improvement, and in some cases complete clearance, of eye soreness in individuals administered the composition described in Example 1.

Example 5

Illustrative Example of Treatment of Watery Eye Condition

Three of the individuals of Example 2 were also assessed for watery eye condition. Results are summarized in Table 6.

Severity of watery eye condition was graded on a scale of 0 to 3. 0 was defined as normal eye condition, 1 was occasional symptoms, 2 was frequent symptoms and 3 was constant watery eye condition. Individuals were instructed to assess amount of tear production by the eyes as a primary indication of watery eye condition.

TABLE 6

Severity of Watery Eye Condition

| Individual No. | Before use | Day 3–5 | Day 5–7 | Day 8–14 | Day 15–21 | Day 22–28 | Day 29–35 | Day 36–42 |
|---|---|---|---|---|---|---|---|---|
| 1 | | | | | | | | |
| 2 | | | | | | | | |
| 3 | | | | | | | | |
| 4 | | | | | | | | |
| 5 | | | | | | | | |
| 6 | | | | | | | | |
| 7 | | | | | | | | |
| 8 | 2 | 2 | 1 | 1 | 1 | | | |
| 9 | 2 | 2 | 1 | 1 | | | | |
| 10 | 2 | 2 | 2 | 1 | 1 | 1 | | |

The results show a clear and significant improvement of watery eye condition individuals administered the composition described in Example 1.

Example 6

Illustrative Example of Treatment of Contact Lens Discomfort

One of the individuals of Example 2 was also assessed for contact lens discomfort. Results are summarized in Table 7.

Severity of contact lens discomfort was graded on a scale of 0 to 3. 0 was defined as normal eye condition, 1 was occasional symptoms, 2 was frequent symptoms and 3 was constant contact lens discomfort. The individual was instructed to assess conditions of dry eye, eye strain/fatigue, eye soreness and/or watery eye (all conditions as defined in the preceding Examples) as primary indications of discomfort associated with the wearing of contact lens.

TABLE 7

Severity of Contact Lens Discomfort

| Individual No. | Before use | Day 3–5 | Day 5–7 | Day 8–14 | Day 15–21 | Day 22–28 | Day 29–35 | Day 36–42 |
|---|---|---|---|---|---|---|---|---|
| 1 | | | | | | | | |
| 2 | | | | | | | | |
| 3 | | | | | | | | |
| 4 | 3 | 3 | 3 | 2 | 1 | 1 | | |
| 5 | | | | | | | | |
| 6 | | | | | | | | |
| 7 | | | | | | | | |
| 8 | | | | | | | | |
| 9 | | | | | | | | |
| 10 | | | | | | | | |

The results indicate that the composition is also effective in treating eye discomfort associated with the wearing of contact lenses.

Example 7

Illustrative Example of Treatment of Eye Discomfort

A randomized, double-blinded and controlled study is performed. A control group is included that uses placebo capsules. Dosage amount and schedule are 1 to 6 capsules (of the composition of Example 1) daily. At least 20 individuals are tested, randomly assigned in approximately equal number to treatment (administered the composition of Example 1) and control groups. They are evaluated to suffer from eye discomfort symptoms, such as dry eye, eye strain/fatigue, eye soreness, and/or watery eye.

The study is carried out for at least 1 week. During the treatment course, a dosage amount selected from the range of 1 to 6 capsules is administered to each individual once or multiple times daily, not exceeding 6 capsules per day. Capsules are administered before or after food consumption.

A clinical questionnaire is used to evaluate individuals' eye discomfort symptoms. A clinical coordinator and/or physician evaluates the individuals' eye discomfort symptoms and fills out the questionnaire. The criteria for assessing severity of symptoms include those described in the preceding Examples. Evaluations can be performed daily, or more or less frequently depending on statistical or clinical (ability to detect or track symptomatic improvements) need.

Assessment of symptoms is divided into 4 grades: (1) clinical cure, as defined as free of symptoms; (2) significant efficacy, as defined as significantly improved symptoms (e.g., reduction of more than 3 points on any one of discomfort scoring scales); (3) efficacy, as defined as partially improved (e.g. reduction of more than 1 point on any one of discomfort scoring scales); and (4) non-efficacy, as defined as no improvement in symptoms.

Example 8

A Second Illustrative Example of Treatment of Eye Discomfort

A multi-center, double-blind, randomized, parallel, placebo-controlled study was conducted. The study was of four weeks in duration. Prior to treatment, subjects were asked to note their average symptom scores, which were recorded to establish an accurate baseline. Two and four weeks following treatment, subjects were asked to record their symptom scores. In this study, the composition of Example 1 was co-administered with an enhancing composition (which by itself is not efficacious in treating eye discomfort conditions, which is disclosed in co-pending application entitled "Compositions And Methods For Enhancing Therapeutic Effects" (U.S. Provisional Application Ser. No. 60/208,990; U.S. pat. application Ser. No. 09/872,082 filed Jun. 01, 2001), which is hereby incorporated in its entirety by reference. Each capsule containing the enhancing composition contained substances described in Table 8 below.

TABLE 8

| SUBSTANCE [Commercial Source] | AMOUNT (mg) |
| --- | --- |
| Xuejie [Min Tong Herb, Oakland, CA] | 133 |
| Yanhusuo [Mayway, Oakland, CA] | 83 |
| Baishaoyao [Qualiherb, Cerritos, CA] | 83 |
| Shanqi [Sun Ten, Irvine, CA] | 250 |
| Gancao [Qualiherb, Cerritos, CA] | 83 |
| White willow bark [Acta, Sunnyvale, CA] | 10 |
| Black cohosh root [Acta, Sunnyvale, CA] | 10 |
| L-carnitine [Acta, Sunnyvale, CA] | 50 |
| Vitamin E (D Alpha-Tocopherol succinate) [Acta, Sunnyvale, CA] | 21.19 |
| Vitamin C [Acta, Sunnyvale, CA] | 30 |

Dosage and Treatment

Subjects were placed on active treatment or placebo for four weeks. During the treatment phase, each subject was administered 2 capsules of the composition of Example 1 and 2 capsules of the enhancing composition of Table 8 two times daily between or after meals for two weeks, followed by 2 capsules of the composition of Example 1 (without the enhancing composition) two times daily between or after meals for another two weeks. The control subjects were administered placebo capsules according to the same treatment and dosage regimen.

Inclusion Criteria

Study subjects were selected based on a number of set criteria, including:
 (1) a natural or corrected visual acuity of 20/25 or better;
 (2) Zone Quick test of greater than 5 mm in 15 seconds;
 (3) Tear Breakup test of greater than 5 seconds;
 (4) have had one of the eye conditions listed below for at least a month, of severity greater than 3 on a subjective 1-10 scale of eye discomfort: Conditions:
  itchy eyes
  red eyes
  burning eyes
  pain
  tearing (watery) eyes
  dry eyes
  sandy (gritty) eyes
  tired/sore/eyestrain or eye fatigue
  contact lens discomfort
  overall eye discomfort Assessment of Treatment Effect (1) Assessment of improvement of abnormal eye symptoms by Tear Breakup Test: Subjects who had abnormal eyes prior to treatment as indicated by a tear breakup test of less than or equal to 10 seconds were assessed by the Tear Breakup Test at two and 4 weeks after treatment. The Tear Breakup Test measures the time between a complete blink and the appearance of the first randomly distributed corneal dry spot. A moistened fluorescein strip is touched lightly against the inferior tarsal conjunctiva. After several blinks, the patient stares ahead without blinking. A cobalt-blue-filtered light is used to illuminate the front surface of the cornea. The time from the blink to the appearance of the black spot (defect) is measured in seconds.

The percentage of subjects showing improvement observed over baseline (prior to treatment) was determined. Results are described in Table 9.

TABLE 9

| Percentage of abnormal eyes that improved | | |
| --- | --- | --- |
|  | 2 weeks | 4 weeks |
| Treated | 77% | 84% |
| Placebo | 58% | 61% |

(2) Assessment of improvement of abnormal eye symptoms by Zone quick test: Subjects who had abnormal eyes prior to treatment as indicated by a Zone quick test showing equal to or less than 20 mm in dye migration were assessed by the Zone quick test at two and 4 weeks after treatment. The Zone Quick test is a minimally invasive test that measures tear volume by use of a special long strand cotton yellow thread that turns red when exposed to tear. The subject is instructed to look straight ahead. The thread is placed one-third of the distance in from the outer canthus of the lower eyelid. The lower lid is gently pulled down and a folded end of thread is placed on the palpebral conjunctiva. The lid is then released. The subject is instructed to continue primary gaze and to blink normally. The thread is removed 15 seconds later, by gently pulling the lower lid down and removing the thread with an upward motion. The red zone of the thread is measured in millimeters, with a measurement of 10 mm or less indicating abnormally low tear volume and a measurement of 20 mm or greater considered normal.

The percentage of subjects showing improvement observed over baseline (prior to treatment) was determined. Results are described in Table 10.

TABLE 10

| Percentage of abnormal eyes that improved | | |
| --- | --- | --- |
|  | 2 weeks | 4 weeks |
| Treated | 77% | 83% |
| Placebo | 38% | 53% |

(3) Assessment of improvement of abnormal eye symptom by corneal staining: Subjects who had abnormal eyes as indicated by corneal staining prior to treatment were assessed by corneal staining at two and 4 weeks after treatment. Corneal staining involves microscopic examination of the eye to evaluate integrity of the corneal epithelium. It involves injection of a fluorescence dye into the eye to obtain an ogmective assessment of inflammation of the conjunctiva.

The percentage of subjects showing improvement observed over baseline (prior to treatment) was determined. Results are described in Table 11.

TABLE 11

| Percentage of abnormal eyes that improved | | |
| --- | --- | --- |
|  | 2 weeks | 4 weeks |
| Treated | 81% | 89% |
| Placebo | 67% | 53% |

The percentages of abnormal eyes that did not improve as assessed by the tests described above were also recorded, and are described in Tables 12, 13 and 14.

TABLE 12

Percentage of abnormal eyes that did not improve by Tear Breakup Test

|  | 2 weeks | 4 weeks |
|---|---|---|
| Treated | 13% | 14% |
| Placebo | 29% | 35% |

TABLE 13

Percentage of abnormal eyes that did not improve by Zone quick test

|  | 2 weeks | 4 weeks |
|---|---|---|
| Treated | 0% | 0% |
| Placebo | 31% | 7% |

TABLE 14

Percentage of abnormal eyes that did not improve by corneal staining

|  | 2 weeks | 4 weeks |
|---|---|---|
| Treated | 19% | 11% |
| Placebo | 0% | 0% |

The percentages of abnormal eyes with a negative response as assessed by the tests described above were also recorded, and are described in Tables 15, 16 and 17.

TABLE 15

Percentage of abnormal eyes with a negative response by Tear Breakup Test

|  | 2 weeks | 4 weeks |
|---|---|---|
| Treated | 8% | 2% |
| Placebo | 13% | 6% |

TABLE 16

Percentage of abnormal eyes with a negative response by Zone quick test

|  | 2 weeks | 4 weeks |
|---|---|---|
| Treated | 23% | 10% |
| Placebo | 6% | 12% |

TABLE 17

Percentage of abnormal eyes with a negative response by corneal staining

|  | 2 weeks | 4 weeks |
|---|---|---|
| Treated | 0% | 0% |
| Placebo | 30% | 46% |

The percentages of normal eyes with a negative response as assessed by the tests described above were also recorded, and are described in Tables 18, 19 and 20.

TABLE 18

Percentage of normal eyes with a negative response by Tear Breakup Test

|  | 2 weeks | 4 weeks |
|---|---|---|
| Treated | 2% | 0% |
| Placebo | 0% | 0% |

TABLE 19

Percentage of normal eyes with a negative response by Zone quick test

|  | 2 weeks | 4 weeks |
|---|---|---|
| Treated | 0% | 7% |
| Placebo | 25% | 27% |

TABLE 20

Percentage of normal eyes with a negative response by corneal staining

|  | 2 weeks | 4 weeks |
|---|---|---|
| Treated | 0% | 0% |
| Placebo | 0% | 0% |

As illustrated in the data presented above, the composition of Example 1 is efficacious in treating various eye discomfort conditions, generally without causing significant adverse side effects.

Although the foregoing invention has been described in some detail by way of illustration and example for purposes of clarity of understanding, it will be apparent to those skilled in the art that certain changes and modifications can be practiced. Therefore, the description and examples should not be construed as limiting the scope of the invention, which is delineated by the appended claims.

What is claimed is:

1. A composition for treating eye discomfort comprising fuling, jueminzi, sang ye, shanyao, shanzhuyu, shudihaung, bilberry, danshen, gouqizhi, juhua, baijili, beta-carotene, copper, gujincao, magnesium, mudanpi, rice flour powder, selenium, vitamin B-2, vitamin C, vitamin E, zexie and zinc.

* * * * *